US006538027B2

(12) United States Patent
Manker et al.

(10) Patent No.: US 6,538,027 B2
(45) Date of Patent: Mar. 25, 2003

(54) COMPOSITIONS COMPRISING RATITE OIL OR ACTIVE FRACTIONS THEREOF AND METHODS OF USING THESE COMPOSITION AS INSECT REPELLENTS

(75) Inventors: Denise C. Manker, Davis, CA (US); Pamela Gail Marrone, Davis, CA (US); Stephen Judd, Davis, CA (US)

(73) Assignee: AgraQuest, Inc., Davis, CA (US)

( * ) Notice: Subject to any disclaimer, the term of this patent is extended or adjusted under 35 U.S.C. 154(b) by 0 days.

(21) Appl. No.: 09/784,927

(22) Filed: Feb. 15, 2001

(65) Prior Publication Data

US 2001/0010813 A1 Aug. 2, 2001

Related U.S. Application Data

(60) Division of application No. 08/914,429, filed on Aug. 19, 1997, now abandoned, which is a continuation-in-part of application No. 08/876,268, filed on Jun. 16, 1997, now Pat. No. 5,929,113, which is a continuation-in-part of application No. 08/849,748, filed on Jun. 12, 1997, now abandoned, which is a continuation-in-part of application No. PCT/US97/04101, filed on Mar. 13, 1997, now abandoned, which is a continuation-in-part of application No. 08/746,894, filed on Nov. 18, 1996, now Pat. No. 5,677,338, which is a continuation-in-part of application No. 08/616,708, filed on Mar. 15, 1996, now Pat. No. 5,626,882.

(51) Int. Cl.[7] ........................ A01N 37/02; A01N 37/06; A01N 37/18; A01N 63/00; A61K 35/12

(52) U.S. Cl. ........................ 514/560; 514/23; 514/25; 514/26; 514/27; 514/32; 514/33; 514/35; 514/42; 514/53; 514/54; 514/182; 514/560; 514/546; 514/547; 514/549; 514/557; 514/558; 514/617; 514/703; 514/705; 514/729; 514/739; 514/919; 424/522; 424/725; 424/742; 424/745; 424/750; 424/761; 424/764; 424/774; 424/777; 424/DIG. 10

(58) Field of Search ........................ 424/522, DIG. 10, 424/725, 742, 745, 750, 761, 764, 774, 777; 514/617, 919, 558, 560, 547, 23, 25, 26, 27, 32, 33, 35, 42, 53, 54, 182, 546, 549, 557, 703, 705, 729, 739

(56) References Cited

U.S. PATENT DOCUMENTS

| | | | |
|---|---|---|---|
| 4,293,422 A | 10/1981 | Still | 210/656 |
| 4,774,081 A | 9/1988 | Flashinski et al. | 514/919 |
| 5,208,209 A | 5/1993 | Otsuji et al. | 503/221 |
| 5,346,922 A | 9/1994 | Beldock et al. | 514/703 |
| 5,431,924 A | 7/1995 | Ghosh et al. | 424/522 |
| 5,472,713 A | 12/1995 | Fein et al. | 424/522 |
| 5,589,181 A | 12/1996 | Bencsits | 424/405 |
| 5,594,029 A | 1/1997 | Bencsits | 514/552 |
| 5,626,882 A | 5/1997 | Marrone et al. | 424/522 |
| 5,677,338 A | 10/1997 | Manker et al. | 514/547 |
| 5,698,227 A | 12/1997 | Rivlin | 424/522 |
| 5,801,196 A | 9/1998 | Manker et al. | 514/547 |
| 5,929,113 A | 7/1999 | Manker et al. | 514/547 |
| 6,103,246 A | * 8/2000 | Tisdale et al. | 424/401 |

FOREIGN PATENT DOCUMENTS

| | | |
|---|---|---|
| EP | 620014 | * 10/1994 |
| WO | WO 92/08470 | 5/1992 |
| WO | WO 97/33594 | 9/1997 |
| WO | WO 98/57542 | 12/1998 |

OTHER PUBLICATIONS

Hwang et al., (1984). "Structure–Activity Relationship of Unsaturated Fatty Acids as Mosquito Ovipositional Repellents," *J. Chem. Ecol.* 10(1):145–151.

PROMT Database Accession No. 96:342230 (Jul. 1, 1996) "Emu Oil Takes the Bite out of Bugs" PR NewsWire, Miami, Florida.

Sharma, V.P. et al., (1993). "Mosquito Repellent Action of Neem (*Azadirachta indica*) Oil" *J. American Mosquito Control Association* 9(3):359–360.

Still, W.C. et al., (1978). "Rapid Chromatographic Technique for Preparative Separations with Moderate Resolution" *J. Organic Chem.* 43:2923–2925.

Watanabe, K. et al., (1993). "New Mosquito Repellent from *Eucalyptus camaldulensis*" *J. Agric. Food Chem.* 42:2164–2166.

Watanabe, K. et al., (1995). "Rotundial, a New Natural Mosquito Repellent from the Leaves of *Vitex rotundifolia*" *Biosci. Biotech. Biochem.* 59(10):1979–1980.

Hsiao, L. L. et al., "Modification of host cell membrane lipid composition by the intra–erythrocytic human malaria parasite *Plasmodium falciparum*," The Biochemical Journal, vol. 274, part 1, Feb. 1991, pp. 121–132.*

* cited by examiner

*Primary Examiner*—John Pak
(74) *Attorney, Agent, or Firm*—Morrison & Foerster LLP

(57) ABSTRACT

This invention provides compositions for repelling insects, particularly biting insects, such as mosquitoes, ticks, and biting flies comprising ratite oil, active fractions of ratite oil obtained by flash chromatography or compositions comprising mixtures of fatty acids found in ratite oil. Also provided are compositions for repelling insects comprising ratite oil, active fractions of ratite oil or compositions comprising mixtures of fatty acids found in ratite oil further comprising at least one additional insect repellent. Methods of repelling insects, particularly biting insects, are provided comprising topically applying ratite oil, active fractions of ratite oil, or compositions comprising mixtures of fatty acids found in ratite oil; or ratite oil, active fractions thereof, or compositions comprising fatty acids found in ratite oil and further comprising at least one additional insect repellent.

15 Claims, 5 Drawing Sheets

FIGURE 3. 1H NMR spectrum of 776 F1

FIGURE 4. 1H NMR spectrum of 776 F2 ions comprising ratite oil or active fractions thereof and methods of using these composition as insect repellents

RELATED APPLICATIONS

This application is a divisional of U.S. application Ser. No. 08/914,429, filed Aug. 19, 1997, now abandoned, which is a continuation-in-part of U.S. Ser. No. 08/876,268, filed Jun. 16, 1997, now U.S. Pat. No. 5,929,113, which is a continuation-in-part of U.S. Ser. No. 08/849,748, filed Jun. 12, 1997, now abandoned, which is the U.S. National Phase filing of PCT/US97/04101, filed Mar. 13, 1997, now abandoned, which is a continuation-in-part of U.S. Ser. No. 08/746,894, filed Nov. 18, 1996, now U.S. Pat. No. 5,677,388, issued Oct. 14, 1997, which is a continuation-in-part of U.S. Ser. No. 08/616,708, filed Mar. 15, 1996 now U.S. Pat. No. 5,626,882, issued May 6, 1997, the disclosures of each of which are incorporated herein by reference in their entirety.

TECHNICAL FIELD

This invention is in the field of topical insect repellents. More particularly, effective, natural and safe biting fly repellents comprising oil from ratites, which include rheas, emus, ostriches, kiwis and cassowaries, active fractions of ratite oil and compositions comprising ratite oil or active fractions thereof and citronella or citronella and saponin are provided. Composition comprising ratite oil or active fractions thereof and at least one other insect repellent are also provided. In addition, compositions for repelling biting insects comprising a mixture of fatty acids are provided. Methods for repelling insects comprising applying such compositions are also provided.

BACKGROUND ART

This invention relates to a compositions and methods for repelling insects, and more particularly to compositions and methods for repelling biting insects such as mosquitoes and biting flies, for example, ceratopogonid flies, using a natural ingredient, oil from ratites, which include rheas, emus, ostriches, kiwis and cassowaries, active fractions of such oils and compositions comprising ratite oil or active fractions thereof and at least one other insect repellent such as citronella or DEET, optionally, further comprising saponin. Also included are compositions for repelling insects comprising a mixture of certain fatty acids and methods for repelling insects comprising application of such compositions comprising certain fatty acids.

Known natural oils that repel insects include rotundial (from the leaves of *Vitex rotundifolia*, Watanabe K et al. (1995) *Biotech Biochem* 59(10):1979–1980); citronella oil (e.g. U.S. Pat. No. 5,346,922); eucalyptus oil (Watanabe et al. (1993) *J. Agric. Food Chem.* 41:2164–2166); neem oil (Sharma V P et al. (1993) *J. American Mosquito Control Association* 9(3):359–360); and oil of *Hedeoma pulgioides*, oil of anisum and oil of chrysanthemum (U.S. Pat. No. 5,208,209). Another natural oil that has repellent activity is saponin (Croda from Sapindus). Saponin has been shown to repel lice and also serves to improve the spreading consistency of repellent compositions and reduce greasiness.

However, the compound most widely used as a topically-applied insect repellent is N,N-diethyl-m-toluamide (DEET). When applied to children's skin, DEET has been implicated in causing convulsions. DEET is also known to react with certain plastics and synthetic rubber and cause skin irritation (Watanabe et al. (1993), supra). As a result of these problems and other side effects, New York State had banned products comprised of 100% DEET.

The active fractions of the naturally-occurring insect repellents are also largely unknown. Methods of resolving heterogeneous compounds into chemical species are well-known in the art. For example, silica gel flash chromatography provides for high speed resolution of organic compounds (see, e.g., U.S. Pat. No. 4,293,422). After separation, the eluted fractions can be recovered and tested for the activity of interest.

Franz Bencsits, U.S. Pat. No. 5,589,181, has reported that certain C1 to C4 fatty acid alkyl esters and fatty alcohols preferably having 5 to 18 carbon atoms have insect repellent activity. Bencsits discloses that the C1 to C4 fatty acid alkyl esters can be obtained from C5 to C9 fatty acids present in rape-seed oil, sunflower oil, peanut oil, peanut butter, soy oil, safflower seed oil, cuphea oil, coconut oil, palm kernel oil, palm oil and fish oil. The fatty alcohols may be obtained from paraffin and/or ethene. Bencsits further discloses that in order to slow down the evaporation of the active substances, the C1 to C4 fatty acid alkyl esters and/or the fatty alcohol, a carrier can be provided consisting of natural or nature-identical vegetal and/or animal oils. Bencsits does not, however, teach or suggest the compositions of the instant invention.

Accordingly, there remains a need for a natural, safe substance that acts to repel insects, particularly biting insects, when topically applied to the skin. The active fraction(s) of such a substance are also needed as are effective compositions comprising ratite oil or active fractions thereof and compositions comprising ratite oil or active fractions thereof in combination with at least one other insect repellent such as citronella, DEET or saponin. Compositions comprising mixtures of fatty acids that effectively repel insects are also needed.

SUMMARY OF THE INVENTION

The present invention provides a method for repelling insects, particularly biting insects, comprising topically applying ratite oil, active fractions of ratite oil, or a composition comprising a mixture of fatty acids to a subject. Methods for repelling insects, particularly biting insects, comprising topically applying compositions comprising ratite oil, active fractions thereof or mixtures of fatty acids and at least one other insect repellent such as citronella or DEET to the skin of a subject are also provided. The invention further provides compositions for repelling biting insects comprising active fractions of ratite oil or a mixture of fatty acids or compositions comprising ratite oil, active fractions thereof or a mixture of fatty acids and at least one other insect repellent such as citronella, DEET or saponin.

MODES FOR CARRYING OUT THE INVENTION

Figure 1:
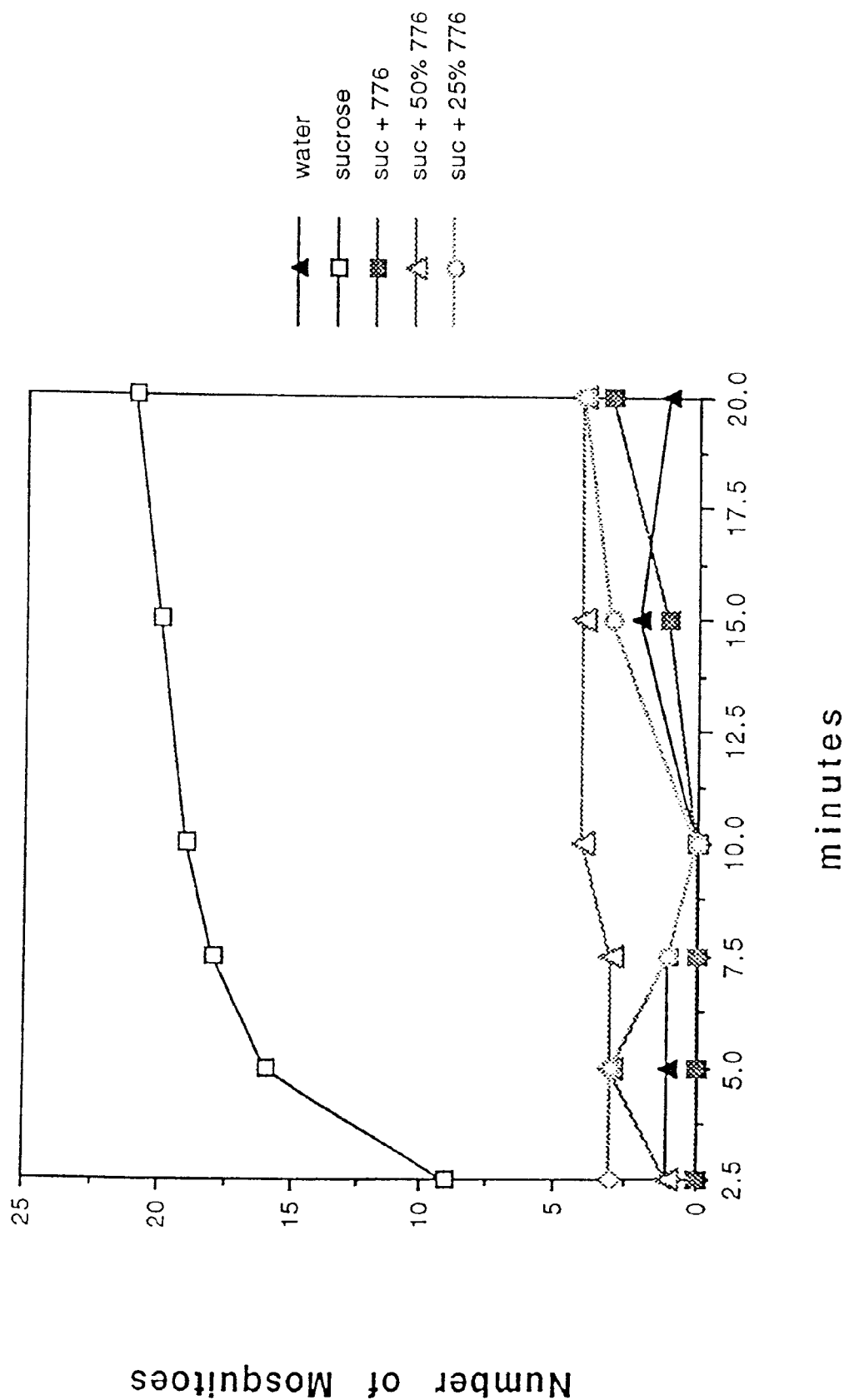
FIG. 1 shows the number of mosquitoes present on filter paper treated with water, sucrose or sucrose and diluted emu oil (sample 776) at 2.5 minute intervals. The solid triangles show water-treated filter paper controls. The open squares show sucrose-treated filter paper. The solid squares show sucrose-treated paper overlaid with undiluted sample 776. The open triangles show sucrose-treated paper overlaid with a 50% dilution of sample 776. The open circles show sucrose-treated paper overlaid with sample 776 diluted to 25%.

Throughout this application, various publications, patents and patent applications are referred to by an identifying citation. The disclosures of these publications, patents and patent applications are hereby incorporated by reference into this application to more fully describe the state of the art to which this invention pertains.

The present invention provides methods of repelling insects, particularly biting insects, using oil from ratites, which include rheas, emus, ostriches, kiwis and cassowaries, and is a natural and safe substance. The invention also includes methods of repelling insects comprising applying active fractions of ratite oils. The present invention also provides compositions for repelling insects comprising fatty acids that have a repellent effect. The invention also provides for methods of repelling insects comprising applying such compositions comprising mixtures of fatty acids topically. In a preferred embodiment, pure ratite oil is applied to the skin. In another preferred embodiment, diluted ratite oil is topically applied. In yet another preferred embodiment, an active fraction of ratite oil is applied to the skin. In a further preferred embodiment, a composition comprising ratite oil or an active fraction thereof and at least one other insect repellent is applied to the skin. Suitable insect repellents that can be combined with ratite oil or an active fraction thereof include, but are not limited to, N,N-diethyl-m-toluamide (DEET) citronella oil, rotundial oil, eucalyptus oil, neem oil, oil of *Hedeoma pulgioides*, oil of anisum, oil of chrysanthemum and saponin.

The present invention further provides compositions for repelling biting insects comprising ratite oil, active fractions of ratite oil or a mixture of fatty acids. Also included are compositions comprising ratite oil, an active fraction thereof or a mixture of fatty acids and at least one other insect repellent. Suitable insect repellents that can be combined with ratite oil, an active fraction thereof or a composition comprising a mixture of fatty acids include, but are not limited to, N,N-diethyl-m-toluamide (DEET), citronella oil, rotundial oil, eucalyptus oil, neem oil, oil of *Hedeoma pulgioides*, oil of anisum, oil of chrysanthemum and saponin.

Compositions comprising ratite oil, an active fraction thereof or a mixture of fatty acids and at least one other insect repellent were found to exhibit surprisingly unexpected synergistic results. The repellent activity of these compositions was much greater than either ratite oil, active fractions of ratite oil, a mixture of fatty acids or the other insect repellent alone. This synergistic effect was also observed with diluted preparations of ratite oil and another insect repellent.

The following examples are presented as a further guide to the practitioner of ordinary skill in the art, and are not to be construed as limiting the invention in any way.

EXAMPLES

Example 1

The Effect of Emu Oil on Frequency of Mosquito Lands and Bites

To determine if emu oil was an effective mosquito repellent, pure emu oil (Zoogen, Inc., Davis, Calif.) was applied to one hand of a volunteer. The other hand was left untreated. Each hand was placed in a nylon mesh cage containing mosquitoes (*Aedes aegypti*) and the number of mosquitoes which landed and/or bit in 30 seconds was recorded. The experiment was performed in duplicate. Results of the experiments were averaged and are summarized in Table 1.

TABLE 1

|  | emu-oil treated hand (lands/bites) | untreated hand (lands/bites) |
| --- | --- | --- |
| Test 1 | 0/0 | 11/11 |
| Test 2 | 1/0 | 26/26 |

These results demonstrate that topically applied emu oil is an effective mosquito repellent. It greatly reduces the number of mosquitoes which land, and completely eliminates biting.

Example 2

The Effectiveness of Emu Oil as a Mosquito Repellent Over Time

To determine how long topically applied emu oil maintains efficacy as a mosquito repellent, the treated hand was exposed to a cage of mosquitoes at 15, 30 and 60 minutes after application. The number of lands and bites were compared at each time point with the untreated hand. Results from duplicate experiments were averaged and are presented in Table 2.

TABLE 2

| Time after application | Number of lands on emu-oil treated hand | Number of lands on untreated hand |
| --- | --- | --- |
| 15 | 4 | 18 |
| 30 | 2 | 12 |
| 60 | 10 | 12 |

These results show that emu oil remains an effective mosquito repellent for at least 30 minutes.

Example 3

The Effectiveness of Diluted Emu Oil

To determine the effectiveness of diluted emu oil, the emu oil was diluted with ethyl acetate to a fixed percentage, applied to one hand and inserted into a mosquito cage. The number of lands were recorded. The experiments were performed in duplicate at each dilution level. Results are shown in Table 3.

TABLE 3

| Percent emu oil | Number of lands Exp't 1 | Number of lands Exp't 2 | Average Number of lands |
| --- | --- | --- | --- |
| 0 | 10 | 9 | 9.5 |
| 0.50 | 10 | 10 | 10 |
| 1.0 | 5 | 5 | 5 |
| 5.0 | 6 | 4 | 5 |
| 10.0 | 4 | 5 | 4.5 |
| 25.0 | 2 | 1 | 1.5 |
| 50.0 | 1 | 1 | 1 |
| 75.0 | 1 | 1 | 1 |
| 100.0 | 0 | 0 | 0 |

These results demonstrate that dilute amounts of emu oil effectively repel mosquitoes. At a dilution as low as 1%, emu oil reduces by one-half the number of mosquitoes which land. At 25% emu oil, the number of mosquito lands drops to one-tenth of lands on an untreated hand. Thus, emu oil is an effective insect repellent at a concentration of 1% or higher.

Example 4

Fractionation of Emu Oil and the Effectiveness of the Fractions

Figure 3:
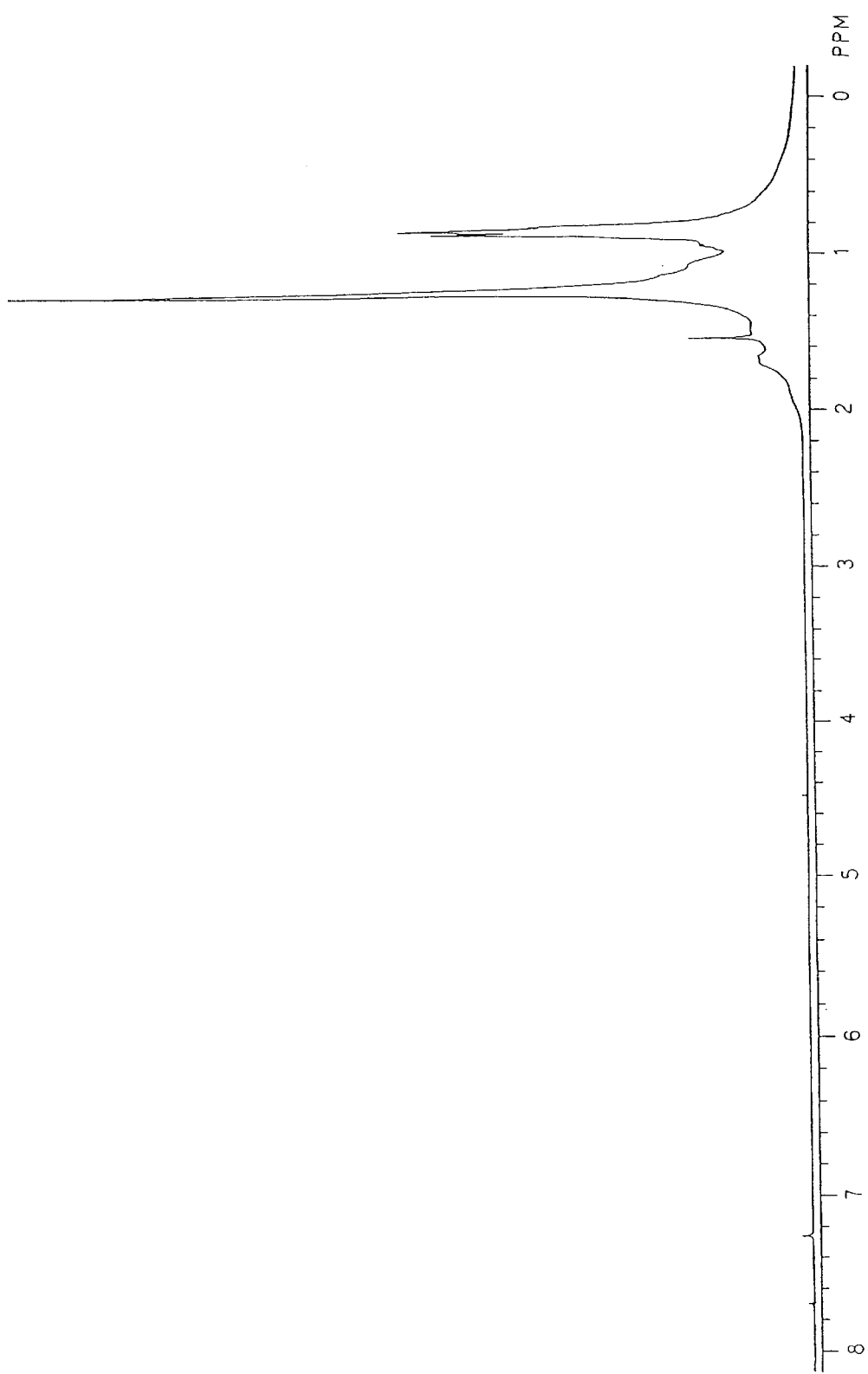
FIG. 3 shows the $^1$H NMR spectrum of the F1 fraction of emu oil.
Figure 4:
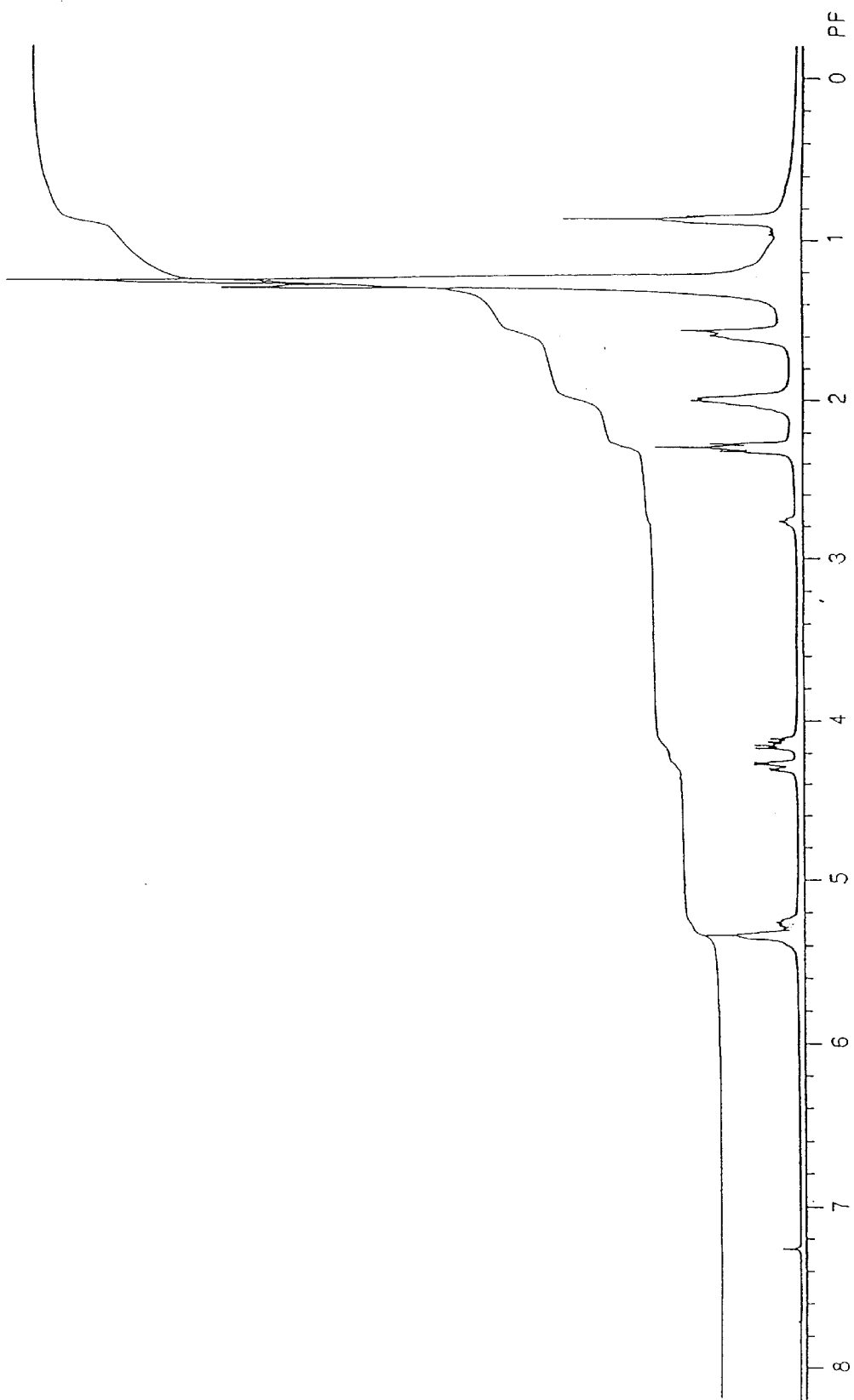
FIG. 4 shows the $^1$H NMR spectrum of the F2 fraction of emu oil.

An 850 mg sample (776) of emu oil was steam-distilled and fractionated using silica flash chromatography (Baker silica gel, 40 µm), essentially as described in Still et al. (1978) *J. Organic Chem.* 43:2923. Two major components of the sample were eluted from the column with 100% hexane and 25% ethyl acetate/hexane. Fractions were analyzed by thin layer chromatography (TLC) on silica plates developed with 50% hexane/ethyl acetate. Components on the TLC plates were observed by exposing the plates to UV light (indicating UV chromophores) and spraying plates with vanillin/sulfuric acid (indicating the presence of higher alcohols, sterols, phenols or essential oils). 430 mg of a clear oil, termed F2, was found to be UV active and reactive to vanillin/sulfuric acid. The second component, 380 mg of a pale yellow oil termed F1, was not UV active and did not stain with vanillin. F1 and F2 fractions were analyzed by $^1$H NMR (300 MHz, $CDCl_3$) as shown in FIGS. 3 and 4.

A mosquito repellent bioassay was performed by treating wedges of filter paper with sucrose overlaid with either an aliquot of the crude sample 776, F1 or F2. Filter paper treated with water or sucrose served as controls. Samples of F1 and F2 were tested at full-strength or diluted with corn oil to 50% or 25% of full-strength. At regular time intervals, the number of mosquitoes which landed and fed on the wedges of filter paper was recorded. Results are shown in FIGS. 1 and 2.

Figure 2:
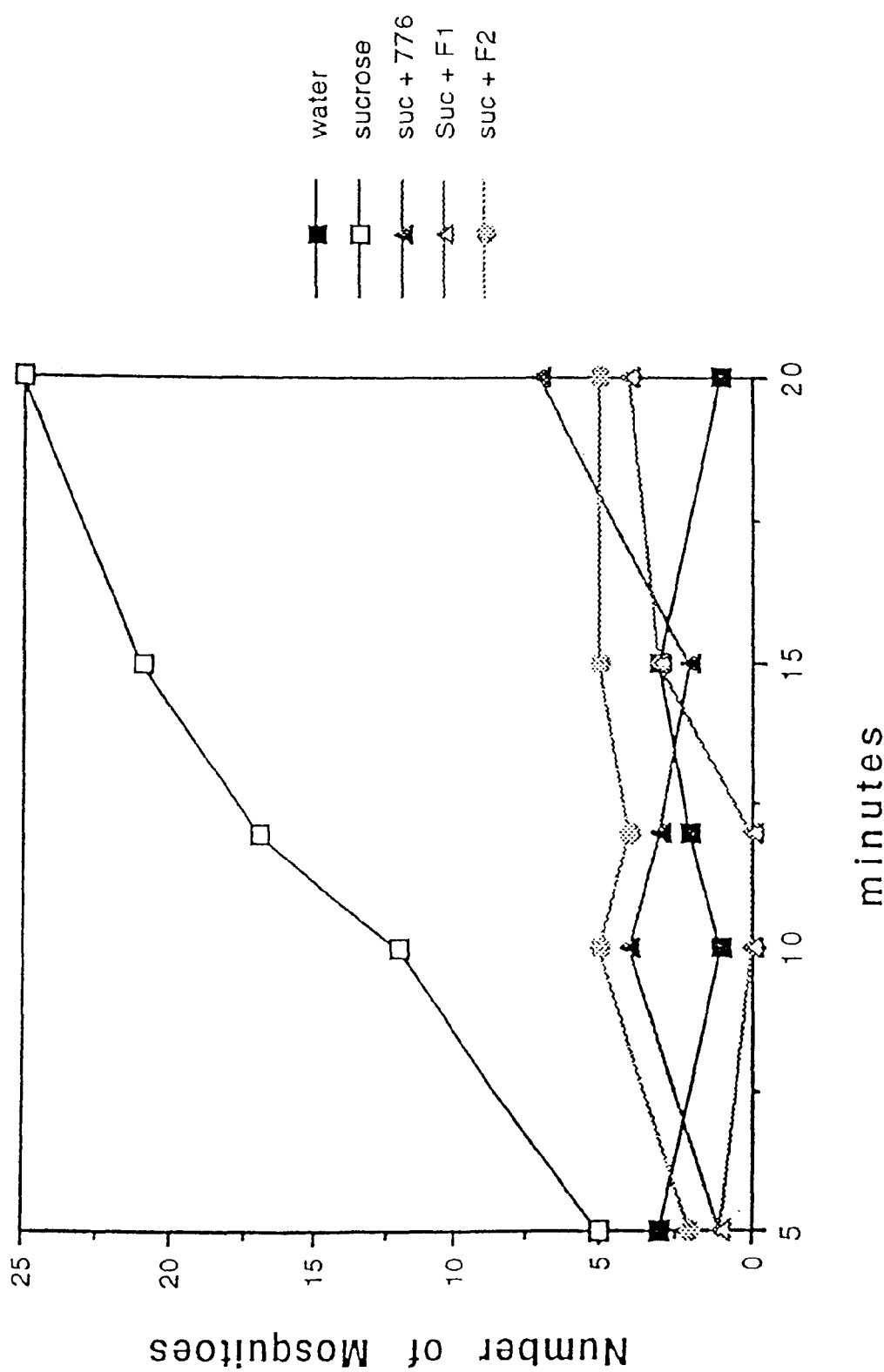
FIG. 2 shows the number of mosquitoes present on filter paper treated with water, sucrose, or sucrose and fractions of sample 776 at 5 minute intervals. The solid squares show water-treated paper. The open squares show sucrose-treated paper overlaid. The solid triangles show sucrose-treated paper overlaid with a sample 776. The open triangles show sucrose-treated paper overlaid with fraction F1. The solid circles show sucrose-treated paper overlaid with fraction F2.

As shown in FIG. 1, even diluted to 25% of full-strength, the crude sample (776) greatly reduces the number of mosquitoes landing on the sucrose paper. In addition, FIG. 2 shows that both the F1 and F2 fractions of sample 776 at full-strength and diluted to 50% or 25% of full-strength were effective in repelling mosquitoes when compared to the sucrose-treated control.

Example 5

The Effect of Emu Oil as a Tick Repellent

To determine if emu oil was an effective tick repellent, a test subject's hands were treated with emu oil while the fingers of the hand were left untreated. As a positive control, Ultrathon (3M, Minneapolis, Minn.) was applied to the hand and the fingers were left untreated. An untreated hand was used as a negative control. Unfed nymphal Western Black-legged ticks were placed on the fingers of the hands and observed as they climbed toward the treated or untreated skin of the hand. Ticks crossing onto the treated skin were scored as "crossing." Those not crossing were scored as "repelled." Ticks were removed after a single score was recorded. Repellency is calculated as the proportion of all trials in which a tick is repelled. For example, 8 repels in 10 trials provides a repellency of 80%. In this study, each subject tested a tick at 15 minute intervals for 2 hours and 15 minutes. The results are shown below:

| | |
| --- | --- |
| Negative control - untreated skin - | 0% repellency |
| Positive control Ultrathon (3M) - | 70% repellency |
| Emu oil - | 40% repellency |

There was no indication that the repellency declined over the two hour test period.

Example 6

The Effect of a Composition of Emu Oil and Citronella on Frequency of Mosquito Bites To determine if citronella would enhance the mosquito repelling effect of emu oil, the repellent activity of emu oil alone and a composition comprising emu oil and citronella (30 drops of 100% oil of citronella/25 mL of pure emu oil) were compared to a positive control, Ultrathon® (3M, Minneapolis, Minn., approximately 31% DEET). Oil of citronella, *Cymbopagon nardus*, was obtained from Aura Cacia, Weaverville, Calif.

Testing was conducted in the Florida Keys, namely Big Pine Key and Little Pine Key. During testing, the air temperature was 24–26° C., with clear skies and slight wind. *Aedes taeniorhynchus* accounted for >99% of mosquitoes that approached or attacked subjects.

In the first study, three subjects applied pure emu oil, one subject applied Ultrathon, and two subjects served as negative controls. In the second study, oil of citronella was added to the emu oil. Three subjects applied the composition comprising emu oil and citronella, two subjects applied Ultrathon, and two subjects served as negative controls. Six of the participants were employees of the Monroe County, Fla., Mosquito Control Service. Treatments were evenly divided among leg and arm surfaces. The surface areas of treated surfaces were calculated for each subject in advance of the application. The test materials were applied at dosage rate of approximately 3 mL/650 square centimeters of surface area.

Test subjects counted and recorded bites in a series of 10 minute periods. Counts were recorded on data sheets. In the first study, the testing period was two hours, with 12 consecutive 10 minute recording periods. In the second study, the test was interrupted during two brief windy periods by the need to move to more productive locales (i.e., places with higher biting rates) within the test sites. As a result, the total testing period including the interruption was two hours and twenty-five minutes.

Figure 5:
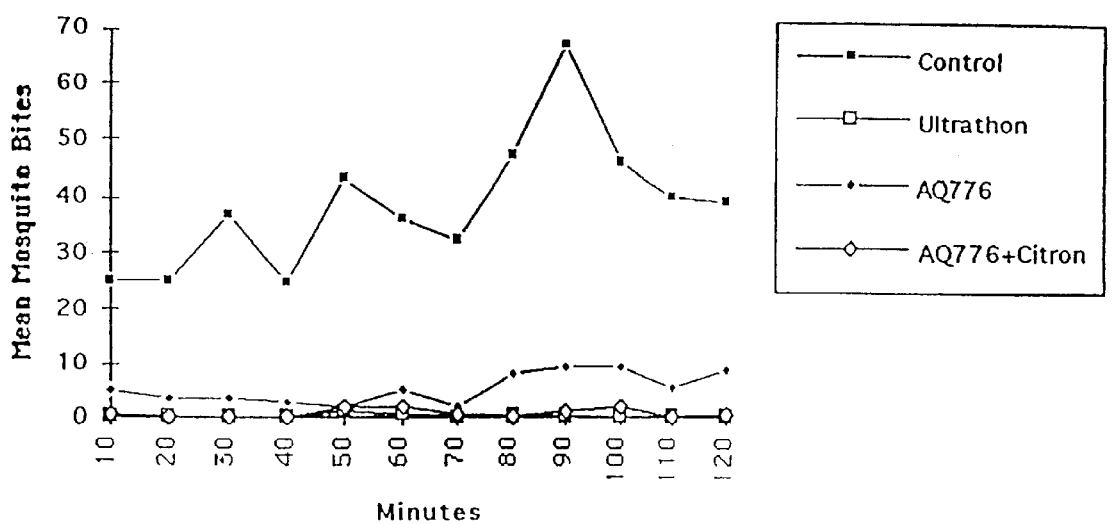
FIG. 5 shows the average number of mosquitoes biting test limbs per ten minute intervals.

Ambient biting rates were measured throughout the study by the subjects with untreated control limbs. The average ambient biting rates were sufficient for testing in both studies and ranged between 17 and 70 bites per 10 minute interval (mean=38.5; see FIG. 5).

Both emu oil and the positive control, Ultrathon, repelled mosquitoes over the test periods. A composition comprising emu oil and oil of citronella was particularly effective as a repellent (see FIG. 5). The repellent properties of emu oil alone reduced the number of bites to an average of 5.7 bites per ten minutes. The composition comprising emu oil and citronella approximated the positive control, Ultrathon, with 0.8 bites per ten minutes for the emu oil/citronella composition compared to 0.2 bites per ten minutes for Ultrathon. Over the testing period, emu oil, a composition comprising emu oil and citronella and Ultrathon substantially reduced biting rates from *Aedes taeniorhynchus*. A composition comprising emu oil and citronella was much more effective than emu oil alone and offers protection comparable to that offered by mosquito repellents registered by the U.S. Environmental Protection Agency (EPA). No pattern of diminishing repellency over time was observed for emu oil and citronella.

Example 7

The Effect of a Composition of Emu Oil, Citronella and Saponin on the Biting Frequency of Ceratopogonid Biting Flies To determine the efficacy of a composition comprising emu oil, citronella and saponin as a biting insect repellent, eight (8) human subjects took part in an experiment wherein three (3) subjects were treated with emu oil alone or emu oil with citronella and saponin. Three other subjects served as the negative controls while two subjects were treated with two commercially available insect repellents, Ultrathon™, a DEET-based repellent, and Treo™, a plant-based repellent. Testing was conducted at three sites: a) on Big Pine Key, Fla.; b) at Fairchild Tropical Gardens, Miami, Fla.; and c) Hopkins Village, Belize, Central America. Temperatures ranged from 21–24° C., the sky was clear and the winds were slight during each testing period.

Two preparations of emu oil were prepared for testing: a) 100% emu oil alone; and b) 20 mL emu oil plus 30 drops of oil of citronella and 2 mL saponin (Croda, from Sapindus).

The two commercially available repellents used as comparative controls were: a) Ultrathon™ (3M®, Minneapolis, Minn., a United States Environmental Protection Agency (EPA)-registered DEET-based product, approximately 32% DEET); and b) Treo™ (Primavera Laboratories, Inc.®, SPF 15 lotion with 0.05% citronella).

The negative control was untreated skin.

The test materials were applied either to the lower arm or lower leg skin of the study subjects. The areas of treated skin surfaces were calculated for each subject in advance of the application. Applications of the test materials, except Ultrathon, were made at a dosage of 3.0 mL/650 cm², a dosage comparable to that used in studies of herbal repellents for EPA registration. Ultrathon was applied at the manufacturer's recommended dosage of 1 mL/650 cm².

Each test subject recorded the number of bites received by ceratopogonid biting flies on treated or control surfaces during sequential sampling periods that began every 10 minutes, the overall test duration being approximately 1 hour. The EPA recognizes 1 hour as the required protection duration for claims of repellency to small biting flies. The results are shown in Table 4 below.

TABLE 4

| FORMULA TESTED | NUMBER OF 10 MINUTE SAMPLES | MEAN NUMBER OF INSECT BITES | NUMBER OF INSECT BITES: STANDARD DEVIATION |
|---|---|---|---|
| Control | 36 | 5.61 | 4.07 |
| emu oil (100%) | 12 | 0.67 | 1.11 |
| emu oil + citronella and saponin | 36 | 0.19 | 0.46 |
| Treo | 12 | 2.75 | 3.49 |
| Ultrathon | 12 | 0 | 0 |

Biting rates were much lower on each of the test materials than with the control. Biting rates with emu oil and with the emu oil, citronella and saponin composition were much lower than with the control and lower than the EPA-registered herbal repellent, Treo. The emu oil, citronella and saponin composition prevented biting altogether in many of the sampling periods, with confirmed bites (a bite followed by another bite within 30 minutes) recorded only on subject 1 in the first sampling period and subject 3 in the third sampling period. Thus, emu oil has a pronounced synergistic effect when combined with a herbal repellent, such as citronella.

Example 8

The Synergistic Repellent Effects of Emu Oil

A preparation of emu oil was prepared wherein the emu oil was diluted to a final concentration of 0.02% with ethanol. OFF! Skintastic™ (S. C. Johnson) was diluted with ethanol to a final concentration of 0.01%. A 1:1 solution (by volume) of the diluted OFF! and the diluted emu oil was prepared. A 1:1:1 solution consisting of 10 mL of the diluted 0.01% OFF!, 10 mL of the diluted 0.02% emu oil, and 10 mL of ethanol was prepared.

In order to determine whether emu oil has an additive and/or a synergistic effect in combination with other insect repellents, these preparations were tested alone and in combination. Each preparation was applied to the hand of a volunteer and exposed to a population of *Aedes aegypti* mosquitoes for 20 seconds. The test was repeated three times for each preparation. Positive control preparations were either 100% emu oil or 100% OFF!. Negative controls were untreated skin. The results of this testing are shown in Table 5 below.

TABLE 5

| NUMBER OF INSECT BITES PER TREATMENT | | | | | | |
|---|---|---|---|---|---|---|
| 0.02% EMU OIL | 0.01% OFF! | 1:1 MIX of 0.02% emu oil and 0.01% OFF! | 1:1:1 MIX of 0.02% emu oil, 0.01% OFF! and ethanol | 100% EMU OIL | 100% OFF! | Untreated Control |
| 4 | 5 | 1 | 0 | 0 | 0 | 5 |
| 4 | 5 | 2 | 0 | 0 | 0 | 5 |

TABLE 5-continued

NUMBER OF INSECT BITES PER TREATMENT

| 0.02% EMU OIL | 0.01% OFF! | 1:1 MIX of 0.02% emu oil and 0.01% OFF! | 1:1:1 MIX of 0.02% emu oil, 0.01% OFF! and ethanol | 100% EMU OIL | 100% OFF! | Untreated Control |
|---|---|---|---|---|---|---|
| 3 | 5 | 1 | 3 | 0 | 0 | 4 |
| mean3.67 | mean5.00 | mean1.33 | mean1.00 | mean0.00 | mean0.00 | mean4.67 |

These results show that diluted emu oil had both an additive and a synergistic repellency effect in combination with other diluted repellents, in this case a DEET-based repellent.

Example 9

The NMR spectra of the active fractions of emu oil characterized in Example 4 above were found to correspond to spectra of fatty acids. Compositions comprising various percentages of certain fatty acids known to be present in emu oil were prepared and tested for repellent activity. Table 6 below shows the chemical composition of one such composition and comparative information vis-à-vis corn oil, which has been previously shown to be non-repellent, and soybean oil, which is a component of an insect repellent recently introduced to the market as BiteBlocker™ (Consep, Inc., Bend, Oreg.). The percentages of fatty acids in corn and soybean oil listed in Table 6 are from deMan, John M, PRINCIPLES OF FOOD CHEMISTRY (Avi Publishing Co., 1980). The percentages of fatty acids in emu oil were obtained from FASTRAX Ratites, Inc., Santa Ynez, Calif. and were published in WO 92/08470 (Ghosh et al.) which reports the anti-inflammatory activity of emu oil.

TABLE 6

| Fatty Acid | Mgs in Mixture | Percent in Mixture | Percent in Commercial Grade Emu Oil | Percent in Pure Emu Oil Reported in WO 92/08470 | Percent in Corn Oil | Percent in Soybean Oil |
|---|---|---|---|---|---|---|
| Myristic Acid (14:0) | 20 | 0.9 | 0.5 | 0.32 | — | Trace |
| Arachidonic Acid (20:4) | 4.2 | 0.2 | — | 0.2 | — | — |
| Palmitic Acid (16:0) | 625 | 28.7 | 23 | 21.3 | 13 | 11 |
| Stearic Acid (18:0) | 222 | 10.2 | 10 | 7.8 | 4 | 4 |
| Linolenic Acid (18:3) | 12.2 | 0.56 | 0.7 | 0.4 | — | 9 |
| Palmitoleic Acid (16:1) | 83 | 3.8 | — | 5.6 | — | — |
| Oleic Acid (18:1) | 1008 | 46.4 | 45 | 54.5 | 29 | 25 |
| Linoleic Acid (18:2) | 200.3 | 9.2 | 10 | 7.2 | 54 | 51 |

Testing was conducted as in previous experiments reported in the foregoing examples. Tests were conducted in the outdoors in a wildlife area in New Mexico in which the predominant species of mosquito is *Aedes vexans*, an aggressive biting insect. Tests were performed in the summer months in the early afternoon (1430–1630 hours, Test 1) and in the late afternoon/early evening (1515–1915 hours, Test 2) near a stream at an elevation of approximately 2500 meters. In two separate tests, four subjects in total applied approximately 2.5 mL of the fatty acid composition shown in Table 6 to one lower arm. The other lower arm of each subject was untreated and served as a control.

Test 1
In Test 1, three subjects were exposed for a period of two hours. Ambient biting was estimated at three (3) bites per minute on each untreated lower arm. No bites were received by any of the test subjects on the treated arm surfaces over the two hour test period.

Test 2
In Test 2, one subject was exposed for a period of four hours. The ambient biting rate per lower arm was measured in each of twenty-four (24) ten (10) minute periods. The ambient biting rate average 0.5 bites per minute and ranged from 0 to 1.5 bites per minute. The test subject received one bite on the treated lower arm surface at approximately 225 minutes after application of the composition. In contrast, the test subject received a total of 116 bites on the untreated control lower arm surface during the 240 minute test period.

Thus, these results demonstrate that compositions comprising mixtures of fatty acids present in ratite oil are effective as insect repellents. The mixtures of free fatty acids comprise about 0.32% to 0.9% myristic acid, about 0.2% arachidonic acid, about 21.3% to 28.7% palmitic acid, about 7.8% to 10.2% stearic acid, about 0.4% to 0.56% linolenic acid, about 3.8% to 5.6% palmitoleic acid, about 46.4% to 54.5% oleic acid, and about 7.2% to 9.2% linoleic acid by weight.

Having now fully described this invention, it will be appreciated by those skilled in the art that the same can be performed within a wide range of equivalent parameters, concentrations and conditions without departing from the spirit and scope of the invention and without undue experimentation. While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows the scope of the appended claims.

What is claimed is:

1. A composition capable of repelling insects comprising a mixture of free fatty acids isolatable from emu oil and at least one additional insect repellent, wherein the mixture of fatty acids comprises about 0.32% to 0.9% myristic acid, about 0.2% arachidonic acid, about 21.3% to 28.7% palmitic acid, about 7.8% to 10.2% stearic acid, about 0.4% to 0.56% linolenic acid, about 3.8% to 5.6% palmitoleic acid, about 46.4% to 54.5% oleic acid and about 7.2%, to 9.2% linoleic acid by weight.

2. The composition of claim 1, wherein the additional insect repellent is a natural oil.

3. The composition of claim 1, wherein the additional insect repellent is selected from the group consisting of rotundial, eucalyptus oil, neem oil, oil of *Hedeoma pulgioides*, oil of anisum and oil of chrysanthemum.

4. The composition of claim 1, wherein the additional insect repellent is selected from the group consisting of N,N-diethyl-m-toluamide (DEET), citronella and saponin.

5. The composition of claim 1, wherein the mixture of fatty acids comprises 0.9% myristic acid, 0.2% arachidonic acid, 28.7% palmitic acid, 10.2% stearic acid, 0.56% linolenic acid, 3.8% palmitoleic acid, 46.4% oleic acid and 9.2% linoleic acid by weight.

6. The composition of claim 1, wherein the fatty acids are isolated from emu oil.

7. The composition of claim 1, further comprising a carrier.

8. A method of repelling insects comprising topically applying a composition comprising a mixture of free fatty acids isolatable from emu oil, wherein the mixture of fatty acids comprises about 0.32% to 0.9% myristic acid, about 0.2% arachidonic acid, about 21.3% to 28.7% palmitic acid, about 7.8% to 10.2% stearic acid, about 0.4% to 0.56% linolenic acid, about 3.8% to 5.6% palmitoleic acid, about 46.4% to 54.5% oleic acid and about 7.2% to 9.2% linoleic acid by weight.

9. The method of claim 8 wherein the composition further comprises at least one additional insect repellent.

10. The method of claim 9 wherein the additional insect repellent is selected from the group consisting of N,N-diethyl-m-toluamide (DEET), citronella and saponin.

11. The method of claim 9, wherein the additional insect repellent is a natural oil.

12. The method of claim 11, wherein the natural oil is selected from the group consisting of rotundial, eucalyptus oil, neem oil, oil of *Hedeoma pulgioides*, oil of anisum and oil of chrysanthemum.

13. The method of claim 8, wherein the mixture of fatty acids comprises 0.9% myristic acid, 0.2% arachidonic acid, 28.7% palmitic acid, 10.2% stearic acid, 0.56% linolenic acid, 3.8% palmitoleic acid, 46.4% oleic acid and 9.2% linoleic acid by weight.

14. The method of claim 8, wherein the fatty acids are isolated from emu oil.

15. The method of claim 8, wherein the composition comprises a carrier.

* * * * *